United States Patent [19]

Enlow

[11] Patent Number: 5,124,472
[45] Date of Patent: Jun. 23, 1992

[54] HYDROLYTICALLY STABLE PHOSPHITES

[75] Inventor: William P. Enlow, Belpre, Ohio

[73] Assignee: General Electric Company, Parkersburg, W. Va.

[21] Appl. No.: 534,230

[22] Filed: Jun. 7, 1990

[51] Int. Cl.$^5$ .............................................. C07F 9/144
[52] U.S. Cl. ................................................... 558/218
[58] Field of Search .................. 568/817; 558/96, 118, 558/218; 524/128

[56] References Cited

U.S. PATENT DOCUMENTS

| | | | |
|---|---|---|---|
| 3,939,229 | 2/1976 | Hechenbleikner et al. | 558/123 |
| 4,064,100 | 12/1977 | Hechenbleikner et al. | 558/85 |
| 4,305,866 | 12/1981 | York et al. | 558/85 |

OTHER PUBLICATIONS

Patent Abstracts of Japan, vol. 13, No. 491 (C-650) [3839], Nov. 7, 1989, p. 87 C 650 corresponding with Japanese Reference No. 1-193371 dated Aug. 3, 1989.

Primary Examiner—Mary C. Lee
Assistant Examiner—Michael G. Ambrose
Attorney, Agent, or Firm—Lowe, Price, LeBlanc & Becker

[57] ABSTRACT

Hydrolytically stable phosphite compositions for melt flow and color stabilization of thermoplastics may be prepared from crude tetrahydroabietyl alcohol. The phosphites may be reacting said alcohol with an organophosphite, such as by transesterification. Other synthesis techniques may also be used.

5 Claims, No Drawings

HYDROLYTICALLY STABLE PHOSPHITES

BACKGROUND OF THE INVENTION

1. Field of the Invention

Hydrolytically stable phosphite compositions, useful for melt flow and color stabilizing a variety of polymeric products, are prepared from a crude tetrahydroabietyl alcohol.

Description of the Prior Art

A large number of organic phosphite compounds have been proposed for use as melt flow stabilizers and secondary antioxidants for thermoplastic molding and extrusion compositions. Some of the more effective phosphites are organic phosphite esters having the formula:

$$P-(OR)_3$$

Where R=alkyl, aryl, alkaryl, aralkyl and substituted alkyl, aryl, alkaryl and aralkyl (and may be the same or different).

Another important class of phosphite esters is based on polyfuctional alcohols such as pentaerythritol and have the formula:

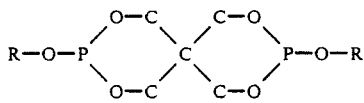

Where R=alkyl, aryl, alkaryl, aralkyl and substituted alkyl, aryl, alkaryl and aralkyl (and may be the same or different). Examples of the latter include distearyl pentaerythritol diphosphite and bis (2,4-di-tert-butyl phenyl) pentaerythritol diphosphite, described, respectively, in U.S. Pat. Nos. 4,064,100 and 4,305,866. The preparation of various trialkyl and trialkenyl phosphites is described in U.S Pat. No. 3,939,229.

A survey of the relevant patent and technical literature failed to uncover any references to phosphites synthesized from abietyl alcohol. Accordingly, the compositions per se are believed to be novel as well as their application as stabilizers for thermoplastic polymers.

DESCRIPTION OF THE INVENTION

In general, the present invention is based on the discovery that hydrolytically stable phosphite compositions may be prepared from crude tetrahydroabietyl alcohol. The phosphites may be synthesized by the transesterification of triphenyl phosphite with an excess of a crude, tetrahydroabietyl alcohol, more specifically a product designated Abitol ® available from Hercules, Inc. Other synthesis techniques may also be used.

Abitol is a commercial product containing about 80% tetrahydroabietyl alcohol with the remainder being a mixture of organic materials, some very complex and difficult to identify chemically. It is made by hydrogenating the rosin acids portion from crude, tall oil fatty acid, the major portion of which is abietic acid. The manufacturer of the crude product provides a hydroxyl number which translates to an apparent molecular weight by hydroxyl equivalence. The apparent molecular weight for the Abitol product used in the examples was 365.

DESCRIPTION OF THE PREFERRED EMBODIMENTS:

The invention may best be understood with reference to the following examples.

EXAMPLE 1

Tris tetrahydroabietyl phosphite was prepared by transesterifying triphenyl phosphite with 10% excess Abitol. A reactor was charged with 1204.5 g Abitol (3.3 mols), 310 g triphenyl phosphite (1 mol) and 2 g sodium methylate as catalyst. The reaction mixture was heated under an inert gas to 120 ° C. and then a vacuum was gradually applied to remove the phenol produced in the reaction. Heating and application of vacuum were continued until reaching 195°-200° C. to less than 1 mm Hg during which time the last of the phenol, the excess Abitol and the non-alcohol components of the Abitol were removed, a total of 390 g of distillate.

The residue was dissolved in n-heptane and filtered through a precoat of Celite. The reaction product was then stripped to 120° C. @<1 mm Hg vacuum. Total recovery was 1100 g or 98% of theoretical yield.

When this product was exposed to 80% relative humidity at ambient temperature, the weight gain was insignificant, thus indicating no hydrolysis. The acid value increased from 0.1 to 2 in a period of 3000 hours. For purposes of comparison, tristearyl phosphite, in a similar test, showed an acid value increase from 0.5 to 27.7 in 352 hours.

In one embodiment, the compounds of the invention have the formula

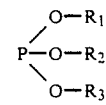

where $R^1$, $R^2$ and $R^3$ are alkyl, aryl, alkaryl, aralkyl, substituted alkyl, substituted aryl or substituted alkaryl, and may be the same or different, and at least one of $R_1$, $R_2$ and $R_3$ is tetrahydroabietyl.

EXAMPLE 2

Bis (tetrahydroabietyl)2,4 di-tert-butyl phenyl phosphite was prepared by first reacting 206 g (1 mol) of 2,4 di-tert-butylphenyl phenol with 310 g (1 mol) of triphenyl phosphite catalyzed with 2 g of sodium methylate (or phenate) to obtain a nominal 2,4 di-tert-butylphenyl diphenyl phosphite. Phenol was distilled through a 20 cm Raschig ring packed column to 150° C. and 30 mm. The reaction terminates at 190° C. at 4 mm after distilling the calculated 1 mol of phenol. The product mixture contained approximately 85% of the desired 2,4,di-tert-butylphenyl diphenylphosphite. The remainder was identified as being predominantly a mixture of bis (2,4 -di-tert-butylphenyl) phenyl phosphite and unreacted triphenyl phosphite.

300 g (0.71 mol) of this crude nominal product was then reacted with 571 g (1.56 mols) of Abitol in a manner similar to Example 1, distilling off the phenol at a terminal condition of 200° C. at less than 1 mm. The product was dissolved in 600 ml of n-heptane and filtered through a Celite precoat to remove the catalyst residues and other solids. The solution was stripped to 205° C. at less than 1 mm distilling off 71 g of condensibles (boiling at above 50° C.). 616.8 g (95% of theoretical yield) of product was recovered as a pale yellow, extremely viscous, liquid material, or a cold flowing glasslike substance, which was determined by IR and elemental analysis to constitute the desired product. The acid number was determined to be less than 0.1 indicating very minimal amounts of acid products, such as those with a phosphorus acid moiety.

EXAMPLE 3

Ethylidene bis 2,4 di-tert-butyl phenol was reacted with $PCl_3$ to yield the cyclic chlorophosphite. The latter was then reacted with Abitol in toluene using triethylamine as the acid acceptor to yield the nominal tetrahydroabietyl ethylidene bis 2,4-di-tert-butylphenyl cyclic phosphite ester. A high melting solid product was obtained after filtration of the amine and removal of the toluene.

EXAMPLE 4

Dichloro pentaerythritol diphosphite (1 mol) was reacted with 2.05 mol of Abitol in toluene using 2.1 mol of triethyl amine as an acid acceptor. The very viscous liquid product, bis abietyl pentaerythritol diphosphite, was obtained after filtering the triethylamine hydrochloride and stripping the toluene.

A wide array of products may be prepared in accordance with the same techniques. One large class would be phosphite esters based on tetrahydroabietyl alcohol (THAA) of the type $(THAA)_n$ [phenyl or substituted phenyl]$_{3-n}$ phosphites. The reaction with various sterically hindered phenols in the ortho position would be preferred, such as 2-tert-alkyl phenol, 2-sec-alkyl phenol, 2,6-di-sec-alkyl phenol and 2-tert-alky-6-n-alkyl phenol. Additionally, use may be made of phenols such as o-nonylated or p-nonylated phenols, all of the above being made by transesterifying triphenyl phosphite.

Additional sterically hindered phenols include compositions such as 2,6 di-tert-butyl 4- Z substituted phenols where Z is alkyl, alkoxy, carboxy, alkyaryl, aryl, aralkyl or virtually any substituent group. The 2,6 di-tert-4 Z substituted phenol may be reacted with $PCl_3$ to produce the dichloride phosphite. One mol of the latter may then be reacted with two mols of Abitol and 2 mols of triethyl amine as the acid receptor resulting in the bis tetrahydro abietyl (2, 6 di-tert-4 Z butylphenyl) phosphite.

Products of the present invention exhibit superior performance in the stabilization of polymers, particularly polyolefins. In order to compare these products with known organophosphite stabilizers, a series of tests was performed. The product prepared in accordance with Example 1 was compared to trinonylphenyl phosphite (TNPP) and tris(2,4 di-tert-butylphenyl) phosphite in a polypropylene resin (Profax ® 6501- Himont). The base formulation contained 100 parts polypropylene resin, 0.1 part of a hindered phenol (Irganox 1010-Ciba-Geigy) and 0.05 parts calcium stearate. All compositions were tested at additions of 0.1 parts per hundred of base resin. The polypropylene (nominal 2 melt flow) was extruded through a 1" Killion extruder using a 3:1 Maddox/ 2:1 screw at 520° F. stock temperature for a total of five passes. Melt flow was measured at the first, third and fifth pass and yellowness index at the first and fifth pass. The results are set forth in Table I below:

TABLE I

| FORMULATION | MELT FLOW | | | YI | |
|---|---|---|---|---|---|
| | 1 | 3 | 5 | 1 | 5 |
| Base | 4.6 | 7.1 | 9.9 | 7.76 | 8.14 |
| TNPP | 2.3 | 2.8 | 3.3 | 8.16 | 8.23 |
| TDTBPP | 2.3 | 2.7 | 3.3 | 7.74 | 7.98 |
| TTHBP | 2.0 | 2.2 | 2.4 | 7.36 | 7.56 |
| BTHBP | 2.1 | 2.4 | 2.8 | 7.30 | 7.53 |

TNPP = Trinonylphenyl phosphite
TDTBPP = tris(2,4-di-tert-butylphenyl) phosphite
TTHBP = tris(tetrahydroabietyl)phosphite
BTHBP = bis(tetrahydroabietyl) 2,4 di-tert-butylphenyl phosphite As the data show, the THBP products of the present invention have excellent stabilization qualities and, as earlier indicated, have almost no tendency to hydrolyze.

The present invention also is a stabilized polymer composition which includes an effective amount of one or more of the tetrahydroabietyl alcohol based phosphite esters described above. An amount of the abietyl alcohol based phosphite esters of the invention is considered to be an "effective amount" when the polymer composition containing the tetrahydroabietyl alcohol based phosphite esters of the invention shows improved stability in any of its physical or color properties in comparison to an analogous polymer composition which does not include a tetrahydroabietyl alcohol based phosphite of the invention. In most polymer compositions, however, it will be preferred that the tetrahydroabietyl alcohol based phosphite be present in an amount equal to about 0.01 to about 2 parts by weight per 100 parts by weight resin (phr). Amounts of about 0.01 to about 1 phr are more preferred, althouqh most compositions will contain about 0.025 phr or more.

The polymer may be any of the polymers known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinylchloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the tetrahydroabietyl alcohol based phosphite esters of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used.

Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene/isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene-propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butdiene, styrene/acrylonitrile, styrene/alkyl methacrylate, styrene/maleic anhydride, styrene/butadiene/ethylacrylate/styrene/acrylonitrile/methylacrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene styrene. Styrenic polymers may additionally or alternatively include graft copolymers of styrene or alpha-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butdiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride-isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally platicized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1, 4-dimethylol-cyclohexane terephthalate, poly-2(2,2,-4(4-hydroxyphenyl)-propane) terphthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following:

1. Antioxidants 1.1 Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alpha-methylcyclohexyl)-4,6-dimethylphenol, 2,6-di-octadecyl-4-methylphenol, 2,4,6-tricyclohexyphenol, 2,6-di-tert-butyl-4-methoxymethylphenol.

1.2 Alkylated hydroquinones, for example, 2,6-di-tert-butyl-4-methoxyphenol, 2,5-di-tert-butyl-hydroquinone, 2,5-di-tert-amyl-hydroquinone, 2,6-diphenyl-4-octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-[4-methyl-6-(alpha-methylcyclohexyl)phenol], 2,2'-methylene-bis-(4-methyl-6-cyclohexylphenol), 2,2'-methylene-bis-(6- nonyl-4-methylphenol), 2,2'-methylene-bis-[6-(alphamethylbenzyl)-4-nonylphenol], 2,2'-methylene-bis-[6-(alpha, alpha-dimethylbenzyl)-4-nonylphenol], 2,2'-methylene-bis-(4,6-di-tert-butylphenol), 2,2'-ethylidene-bis-(6tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-[3,3-bis-(3'-tert-butyl-4'-hydroxyphenyl)-butyrate],di-(3-tert-butyl-4-hydroxy-5-methylphenyl)-dicyclopentadiene, di-[2-(3'-tert-butyl-2'hydroxy-5'methyl-benzyl)-6-tert-butyl-4-methylphenyl]-terephthalate.

1.5 Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiolterephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, dioctadecyl 3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate.

1.6 Acylaminophenols, for example, 4-hydroxy-lauric acid anilide, 4-hydroxy-stearic acid anilide, 2,4-bisoctylmercapto-6-(3,5-ter-butyl-4-hydroxyanilino)-s-triazine, octyl-N-(3,5-di-tert-butyl-4-hydroxyphenyl)-carbamate.

1.7 Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, di-hydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)-hexamethylendiamine, N,N'-di-(3,5-di-tert-butyl-4-hydroxyphenylpropionyl)-trimethylenediamine, N,N'-di-(3,5-di-tert-butyl-4-hydroxyphenylpropionyl)-hydrazine.

2. UV absorbers and light stabilizers.

2.1 2-(2'-hydroxyphenyl)-benzotriazoles, for example, the 5'methyl-,3'5'-di-tert-butyl-,5'-tert-butyl-,5'(1,1,3,3-tetramethylbutyl)-,5-chloro-3',5'-di-tert-butyl-, 5-chloro-3'tert-butyl-5'-methyl-,3'sec-butyl-5'tert-butyl-,4'-octoxy,3',5'-ditert-amyl-,3',5'-bis-(alpha,alpha-dimethylbenzyl)-derivatives.

2.2 2-Hydroxy-benzophenones, for example, the 4-hydroxy-,4-methoxy-,4-octoxy,4-decyloxy-,4-dodecyloxy-,4-benzyloxy,4,2',4'-trihydroxy-and 2'hydroxy-4,4'-dimethoxy derivative.

2.3 Esters of substituted and unsubstituted benzoic acids for example, phenyl salicylate, 4-tert-butylphenylsalicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di -tert-butyl-4-hydroxybenzoate.

2.4 Acrylates, for example, alpha-cyano-beta, betadiphenylacrylic acid ethyl ester or isooctyl ester, alphacarbomethoxy-cinnamic acid methyl ester, alpha-cyano-betamethyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

2.5 Nickel compounds, for example, nickel complexes of 2,2'-thio-bis[4-(1,1,1,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis-(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis-(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate; 1-hydroxy-2,2,6,6-tetramethyl-4-benzoxypiperidine; 1-hydroxy-2,2,6,6-tetramethyl-4-(3,5-ditert-butyl-4-hydroxy hydrocinnamoyloxy)-piperidine; and N-(1-hydroxy-2,2,6,6-tetramethyl-piperidin-4-71)-epsiloncaprolactam.

2.7 Oxalic acid diamides, for examples, 4,4'-dioctyloxy-oxanilide, 2,2'-di-octyloxy-5,5'-di-tert-butyloxanilide, 2,2'-di-dodecyloxy-5,5'di-tert-butyl-oxanilide, 2-ethoxy-2'-ethyl-oxanilide, N,N'-bis(3-dimethylaminopropyl)-oxanilide, 2-ethoxy-5-tert-butyl-2'-ethyloxanilide and its mixture with 2-ethoxy-2'ethyl-5,4-ditertbutyloxanilide and mixtures of ortho- and paramethoxy- as well as of o-and p-ethoxy-disubstituted oxanilides.

3. Metal deactivators, for example, N,N'- diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tertbutylphenyl) pentaerythritol diphosphite tristearyl sorbitol triphosphite, and tetrakis (2,4-di-tert-butylphenyl) 4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, Zn stearate, Mg strearate, Na ricinoleate and K palmitate, antimony pyrocatecholate or zinc pyrocatecholate.

8. Nucleating agents, for example, 4-tert-butylbenzoic acid, adipic acid, diphenylacetic acid.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-[N,N-dibenzylaminoxy]propanoate; ethyl-3-[N,N-dibenzylaminoxy]propanonoate; 1,6-hexamethylene-bis[3-N,N-dibenzylaminoxy)proponoate];methyl-[2-(methyl)-3(N,N-dibenzylaminoxy)propanoate]; octadecyl-3-[N,N-dibenzylaminoxy]propanoic acid; tetrakis[(N,N-dibenzylaminoxy)ethyl carbonyl oxymethyl]methane; octadecyl-3-[N,N-diethylaminoxy]-propanoate; 3-[N,N-dibenzylaminoxy]propanoic acid potassium salt; and 1,6-hexamethylene bis[3-(N-allyl-N-dodecyl aminoxy)propanoate].

11. Other additives, for example, plasticizers, lubricants, emulsifiers, pigments, optical brighteners, flameproofing agents, anti-static agents, blowing agents and thiosynergists such as dilaurythiodipropionate or distearylthiodipropionate.

Hindered phenolic antioxidants may also be present in the polymer composition. Use of abietyl organophosphites of the present invention may result in enhanced polymer protection by reducing the formation of color resulting from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-N-octadecyl 3,5-di-tert-butyl-4-hydroxybenzyl-phosphonate, 1,3,5-tris(3,5-di-tert-butyl-4-hydroxybenzyl-)isocyanurate, thiodiethylene bis(3,5-di-tertbutyl-4-hydroxyhydrocinnamate), 1,3,5-trimethyl-2,4,6-tris(3,5-ditert-butyl-4-hydroxybenzyl)benzene, 3,6-di-9 oxaoctamethylene bis(3-methyl-5-tert-butyl-4-hydroxyhydrocinnamate), 2,6-di-tert-butyl-p-cresol,2,2'-ethylidene-bis(4,6-di-tert-butylphenol),1,3,5-tris-(2,6-dimethyl-4-tert-butyl-3-hydroxybenzyl) isocyanurate. 1,1,3-tris-(2-methyl-4-hydroxy-5-tert-butylphenyl)butane, 1,3,5-tris-[2-(3,5-di-tert-butyl-4-hydroxyhydrocinnamoyloxy)ethyl]-isocyanurate, 3,5-di(3,5-di-tert-butyl-4-hydroxybenzyl)-mesitol, hexa-methylene bis(3,5-ditert-butyl-4-hydroxyhydrocinnamate), 1-(3,5-ditertbutyl-4-hydroxyanilino)-3,5-di(octylthio)-s-triazine, N,N'-hexamethylene-bis(3,5-di-tert-butyl-4-hydroxyhydrocinnamamide), calcium bis (ethyl-3,5-di-tert-butyl-4-hydroxybenzylphosphonate), ethylene bis[3,3-di(3-tertbutyl-4-hydroxyphenyl)butyrate], octyl 3,5-di-tertbutyl-4-hydroxybenzylmercaptoacetate, bis(3,5-di-tertbutyl-4-hydroxyhydrocinnamoyl)hydrazide, and N,N'-bis-[2-(3,5-tertbutyl-4-hydroxyhydroxocinnamoyloxy)-ethyl]-oxamide, and preferably neopentanetetrayl tetrakis(3,5-di-tert-butyl-4-hydroxyhydrocinnamate), N-octadecyl 3,5-di-tert-butyl-4-hydroxyhydrocinnamate, 1,3,5-trimethyl-2,4,6-tris(3,5-ditert-butyl-4-hydroxybenzyl)benzene,1,3,5-tris-(3,5 ditert-butyl-4-hydroxybenzyl)isocyanurate, 2,6-di-tert-butyl-p-cresol or 2,2'-ethylidene-bis(4,6-di-tert-butylphenol).

Other additives, such as oxazapholidines, may additionally or alternatively be present.

Likewise, the instant compounds prevent coor formation when hindered amine light stabilizers are present, such hindered amines including bis(1,2,2,6,6-pentamethyl-4-piperidyl)-2-N-butyl-2-(3,5-di-tert-butyl-4hydroxybenzyl)malonate; bis(2,2,6,6-tetramethyl-4-piperidyl) sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tertramethyl-4-piperidyl)hexamethylene diamine.

Consistent with the invention, the abietyl alcohol based phosphite esters of the invention may be added to the polymer at any time prior to or during fabrication into articles and may be combined with the polymer by any of a variety of means known in the art, such as by preblending or by being fed directly into fabrication equipment.

The preceding examples are set forth to demonstrate specific embodiments of the invention and are not intended to limit the scope of the presently claimed compositions. Additional embodiments and advantages within the scope of the claimed invention will be apparent to one of ordinary skill in the art.

What is claimed is:

1. A tetrahydrobietyl organiphosphite ester, wherein the phosphorus atom of the organophosphite ester is not part of a heterocyclic ring.

2. A transesterification reaction product of tetrahydrobietyl alcohol and an organophosphite wherein the phosphorous atom of the organophosphite ester is not part of a heterocyclic ring in said product.

3. A compound having the formula:

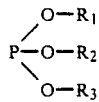
where $R_1$, $R_2$ and $R_3$ are alkyl, aryl, alkaryl or aralkyl, and may be the same or different, and at least one of $R_1$, $R_2$ and $R_3$ is tetrahydroabietyl.
4. Tris(tetrahydrobietyl)phosphite.
5. Bis(tetrahydroabietyl)2,4-di-tert-butylphenyl phosphite.
* * * * *